(12) United States Patent
Metz

(10) Patent No.: US 9,765,021 B2
(45) Date of Patent: Sep. 19, 2017

(54) PROCESS FOR FLUORINATION OF SULPHONYL HALIDE COMPOUNDS

(71) Applicant: RHODIA OPERATIONS, Paris (FR)

(72) Inventor: François Metz, Irigny (FR)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 14/901,473

(22) PCT Filed: Jul. 3, 2014

(86) PCT No.: PCT/EP2014/064183
§ 371 (c)(1),
(2) Date: Dec. 28, 2015

(87) PCT Pub. No.: WO2015/001020
PCT Pub. Date: Jan. 8, 2015

(65) Prior Publication Data
US 2016/0368866 A1    Dec. 22, 2016

(30) Foreign Application Priority Data

Jul. 4, 2013 (FR) .................... 13 01593

(51) Int. Cl.
*C07C 303/38*      (2006.01)
*C07C 303/02*      (2006.01)
*C07C 311/09*      (2006.01)

(52) U.S. Cl.
CPC .......... *C07C 303/38* (2013.01); *C07C 303/02* (2013.01); *C07C 311/09* (2013.01)

(58) Field of Classification Search
CPC ... C07C 303/02; C07C 303/38; C07C 309/06; C07C 309/80; C07C 309/81; C07C 311/48; C07C 303/08; C07C 309/86; C07C 17/093; C07C 17/10; C07C 17/20; C07C 17/202; C07C 17/206; C07C 17/208
USPC ..... 562/30, 825, 826, 828, 831, 834; 564/94
See application file for complete search history.

(56) References Cited

U.S. PATENT DOCUMENTS

| | | | |
|---|---|---|---|
| 2,276,097 A | 3/1942 | Salzberg | |
| 2,732,398 A | 1/1956 | Brice et al. | |
| 3,920,738 A * | 11/1975 | Martin | C07C 303/22 562/825 |
| 4,091,043 A * | 5/1978 | Ohsaka | C07C 17/206 570/170 |
| 4,311,863 A * | 1/1982 | Gumprecht | C07C 17/208 570/170 |
| 5,723,664 A | 3/1998 | Sakaguchi et al. | |
| 6,723,874 B1 | 4/2004 | Palsherm et al. | |
| 2008/0108853 A1* | 5/2008 | Nappa | B01J 23/26 570/161 |
| 2009/0318689 A1* | 12/2009 | Franczyk, II | C07D 295/13 544/121 |

FOREIGN PATENT DOCUMENTS

| | | | |
|---|---|---|---|
| CN | 101456832 A | | 6/2009 |
| DE | 936 090 C | | 12/1955 |
| DE | 936090 | * | 12/1955 |
| DK | 907 775 C | | 3/1954 |
| RU | 2183621 | * | 6/2002 |

OTHER PUBLICATIONS

Machine generated English language translation of Scherer, DE 936090, 1955, p. 1-2.*
Machine generated English language translation of Hoechst, DE 907775, 1954, p. 1-4.*
Il'chenko ("Product Class 15: Tetraheterosubstituted Methane with a Carbon-Halogen Bond" Science of Synthesis, 4.0 version, Section 18.15, vol. 18, 2005, p. 1135-1201).*
Machine generated English language translation of Gup, RU 2183621, 2002, p. 1-12 (including reaction structures obtained from SciFinder).*
Cox ("Anhydrous Tetrabutylammonium Fluoride: A Mild but Highly Efficient Source of Nucleophilic Fluoride Ion" J. Org. Chem., 1984, 49, p. 3216-3219).*
Kageyama, H. et al., "Sulfonyl Chloride as a Disopsable Electron Withdrawing Substituent in Halex Fluorinations", Journal of Fluorine Chemistry, Jan. 1, 2000, Elsevier, NL; vol. 101, Nr: 1, pp. 85-89.
Drabowicz J. et al., "Product Class 1: Alkanesulfonic Acids and Acyclic Derivatives," Science of Synthesis, Jan. 1, 2007; Stuttgart: Georg Thieme Verlag, DE; vol. 39, pp. 17-122.

(Continued)

*Primary Examiner* — Jafar Parsa
*Assistant Examiner* — Amy C Bonaparte

(57) ABSTRACT

The preparation is described of a compound of formula (I) comprising an —$SO_2F$ function by reacting a compound of formula (II) with a fluorinating agent selected from hydrofluoric acid and an ionic fluoride of a monovalent or divalent cation:

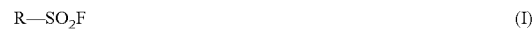

$$R\text{—}SO_2F \qquad\qquad (I)$$

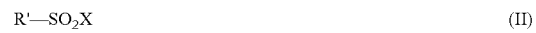

$$R'\text{—}SO_2X \qquad\qquad (II)$$

where R is selected from the groups R1, R2 and R3:
R1=—$C_nH_aF_b$ with n=1-10, a+b=2n+1, b≥1;
R2=—$C_xH_yF_z$—$SO_2F$ with x=1-10, y+z=2x and z≥1;
R3=φ-$C_cH_hF_f$ with c=1-10; h+f=2c and f≥1;
where R' is selected from the following groups R'1, R'2 and R'3:
R'1=—$C_nH_aX_b$ with n=1-10, a+b=2n+1, b≥1;
R'2=—$C_xH_yX_z$—$SO_2X$ with x=1-10, y+z=2x and z≥1;
R'3=φ-$C_cH_hX_f$ with c=1-10; h+f=2c and f≥1; φ denoting a phenyl group;
X=Cl, Br.

9 Claims, No Drawings

(56) References Cited

OTHER PUBLICATIONS

Sartori, P. et al., "Die Elektrofluorierung Von Alpha-Chlorethylsulfochlorid," Journal of Fluorine Chemistry, Jan. 1, 1981, Elsevier, NL; vol. 18, Nr: 2, pp. 131-141.
Sartori, P. et al., "Die Elektrofluorierung Von Chlormethylsulfochlorid," Journal of Fluorine chemistry, 1980-09-01, Elsevier, NL; vol. 16, Nr: 3, pp. 265-276.

* cited by examiner

PROCESS FOR FLUORINATION OF SULPHONYL HALIDE COMPOUNDS

This application is a U.S. national phase entry under 35 U.S.C. §371 of International Application No. PCT/EP2014/064183, filed on Jul. 3, 2014, which claims priority to French Application No. 1301593, filed on Jul. 4, 2013. The entire contents of these applications are explicitly incorporated herein by this reference.

The present invention relates to the field of the fluorination of halogenated compounds, generally of chlorinated compounds, bearing an —$SO_2X$ function where X is a halogen other than fluorine. One subject of the invention is in particular the preparation of compounds of sulfonyl fluoride type such as alkylsulfonyl fluorides or benzylsulfonyl fluorides. More specifically, one subject of the present invention is a process for preparing trifluoromethanesulfonyl fluoride ($CF_3SO_2F$).

Sulfonyl fluoride compounds are intermediates that are particularly advantageous for the synthesis of sulfonimide compounds and compounds bearing a sulfonic acid function, which are high value-added products.

It is known to prepare compounds of sulfonyl fluoride type and in particular trifluoromethanesulfonyl fluoride by electrofluorination of mesyl fluoride $CH_3SO_2F$ (U.S. Pat. No. 4,927,962) or by fluorination of a trifluorosulfinate of a monovalent cation. These prior processes, even though they result in satisfactory performances, suffer from an implementation that is complex and costly (in the case of electrofluorination) and/or that requires steps to be put in place that involve CMR (carcinogenic, mutagenic and reprotoxic) solvents, in particular DMF.

One objective of the invention is therefore to provide a process for preparing sulfonyl fluoride compounds that makes it possible to avoid the drawbacks of the prior art processes. In particular, one objective of the invention is to propose a simplified process for preparing compounds of sulfonyl fluoride type that is cleaner in terms of toxicity of the chemical agents involved and that is more economical. Another objective of the invention is to propose a non-electrochemical process. Yet other objectives will become apparent on reading the invention that follows.

One subject of the present invention is a non-electrochemical process for preparing a fluorinated compound of formula (I) comprising at least one —$SO_2F$ function, characterized in that the compound of formula (I) is prepared by reacting a compound of formula (II) with at least one fluorinating agent selected from hydrofluoric acid and an ionic fluoride of a monovalent or divalent cation:

R—$SO_2F$ (I)

where R is selected from the following groups R1, R2 and R3:
R1=—$C_nH_aF_b$ with n=1-10, a+b=2n+1, b≥1; preferably n=1, a=0, b=3;
R2=-$C_xH_yF_z$—$SO_2F$ with x=1-10, y+z=2x and z≥1;
R3=φ-$C_cH_hF_f$ with c=1-10; h+f=2c and f≥1; φ denoting a phenyl group;

R'—$SO_2X$ (II)

where R' is selected from the following groups R'1, R'2 and R'3:
R'1=—$C_nH_aX_b$ with n=1-10, a+b=2n+1, b≥1;
R'2=—$C_xH_yX_z$—$SO_2X$ with x=1-10, y+z=2x and z≥1;
R'3=φ-$C_cH_hX_f$ with c=1-10; h+f=2c and f≥1; φ denoting a phenyl group;
X being a halogen atom selected from chlorine and bromine.

The preparation process according to the invention is a non-electrochemical fluorination process. Electrofluorination processes are therefore excluded from the invention.

In accordance with the process according to the invention, the radicals R1 and R'1 advantageously have a value of n between 1 and 5, very preferably between 1 and 3. Preferably, n is equal to 1. Preferably, the radicals R1 and R'1 are perhalogenated so that b=3 and a=0. The radicals R2 and R'2 advantageously have a value of x between 1 and 5, very preferably between 1 and 3. Preferably, x is equal to 1. The radicals R3 and R'3 advantageously have a value of c between 1 and 5, preferably between 1 and 3. Preferably, c is equal to 1. The phenyl group φ present in the radicals R3 and R'3 may be substituted with one or more hydroxyl, alkyl, alcohol, thiol, amide or halogen groups and/or by a group —$C_xH_yX_z$—$SO_2X$ with x=1-10, y+z=2x and z≥1, X being a halogen atom selected from chlorine and bromine.

Very preferably, the radical R of the compound (I) prepared according to the process of the invention is the radical R1 wherein n=1, a=0 and b=3, or n=1, a=1, b=2 or else n=1, a=2 and b=1. The compounds of formula $CF_3SO_2F$, $CHF_2SO_2F$ and $CH_2FSO_2F$ are thus respectively prepared from the compounds of formula (II) respectively having the formulae $CX_3SO_2X$ (n=1, a=0 and b=3 in R'1), $CHX_2SO_2X$ (n=1, a=1, b=2 in R'1) and $CH_2XSO_2X$ (n=1, a=2 and b=1 in R'1), where X is bromine or chlorine, preferably chlorine.

Furthermore, a non-electrochemical process is described for preparing a fluorinated compound of formula $SO_2F_2$ characterized in that this compound is prepared by reacting a compound of formula $SO_2X_2$ with at least one fluorinating agent selected from hydrofluoric acid and an ionic fluoride of a monovalent or divalent cation, X being a halogen atom selected from chlorine and bromine.

The process according to the invention can be carried out in the gas phase or in the liquid phase. Preferably, said process is carried out in the gas phase.

According to the preferred embodiment of the process of the invention, according to which it is carried out in the gas phase, the fluorinating agent used for reacting with the compound of formula (II) is hydrofluoric acid.

The preparation process according to the invention, carried out in the gas phase in the presence of hydrofluoric acid, uses at least one fluorination catalyst. Said fluorination catalyst, used in the gas phase fluorination process, is in particular selected from the catalysts comprising, or consisting of, chromium, zinc, nickel, a mixture of chromium and zinc or a mixture of chromium and nickel.

The fluorination catalyst may in particular be a chromium-based catalyst. The catalyst used is a bulk chromium oxide (that is to say a catalyst comprising only the metallic element and oxygen) or preferably comprises oxides, halides, oxyhalides or mineral salts of chromium, optionally doped with a metallic element such as for example nickel, cobalt, magnesium and zinc. It is preferably a chromium oxide, a chromium fluoride or a chromium oxyfluoride, which may optionally be doped with a metallic element, for example nickel or zinc.

The fluorination catalyst may be subjected to an activation via a heat treatment. In particular, the activation may take place during the fluorination process. The temperature is advantageously chosen between 100° C. and 400° C., preferably between 200° C. and 300° C.

Use is in particular made of chromium in the form of oxides with different degrees of oxidation and/or in the form of hydroxides in powder or gel form.

It is possible to use an activated chromium(III) oxide prepared, for example, by precipitation of water-soluble chromium(III) salts, such as, for example, chlorides, nitrates, acetates or sulfates, using an aqueous solution of ammonium hydroxide or using an aqueous solution of an alkali metal hydroxide, preferably sodium or potassium hydroxide. The precipitate is dried at around 110° C. and calcined at a temperature below 700° C., preferably between 200° C. and 600° C. Chromium(III) is understood to mean chromium in the (III) oxidation state.

Anhydrous chromium oxide may be obtained by calcination of inorganic chromium salts, such as ammonium chromate or chromium nitrate, or by calcination of organic chromium salts, such as, for example, chromium oxalates or formates, at a temperature between 200° C. and 500° C., preferably between 250° C. and 450° C., and more preferably still between 250° C. and 400° C., under a nitrogen atmosphere.

The fluorination catalyst may also be a catalyst of Cr—Ni type, with a valency of the chromium of between 2 and 6 and a valency of the nickel of between 0 and 2, the amount of nickel, expressed as an atomic percentage, representing from 0.1% to 50%. A method of preparing this catalyst consists in thermally decomposing, separately or as a mixture, one or more organic chromium salts (for example oxalate) and a salt or several salts of nickel (for example oxalate) and shaping the mixture. The thermal decomposition generally takes place between 200° C. and 600° C., under an inert gas atmosphere, for example a nitrogen atmosphere.

The shaping of the catalyst obtained may be carried out, under non-oxidizing conditions, for example by extrusion, then the shaped product is dried at around 80° C.-150° C. and then calcined at 200° C.-600° C., under an inert atmosphere.

A catalyst of Cr—Mg type may also be used. It may be obtained in particular by mixing a chromium salt (for example nitrate) in solution with a magnesium oxide or hydroxide, and prolonged drying for between 12 and 24 hours, for example at 100° C.

The fluorination catalyst may also be a catalyst based on chromium and zinc. The catalyst used is a bulk zinc or preferably comprises oxides, halides, oxyhalides or mineral salts of zinc, optionally doped with a metallic element such as for example nickel, cobalt or magnesium.

The fluorination catalyst may also be a nickel-based catalyst. The catalyst used is a bulk nickel or preferably comprises oxides, halides, oxyhalides or mineral salts of nickel, optionally doped with a metallic element such as for example zinc, cobalt or magnesium.

In the fluorination catalyst of the invention, the active phase may be introduced in a finely divided form or else shaped or deposited on a support. Mention may be made, as examples of supports, of silica, alumina, partially or completely fluorinated alumina, zirconia or titanium oxide. Preferably, the catalyst is deposited on a support in a proportion of from 0.2% to 15% of the weight of the catalyst. The supported catalysts are prepared according to processes well known to a person skilled in the art and in particular by incipient wetness impregnation or co-impregnation onto the support of metallic precursors dissolved in a suitable volume of water.

The catalysts may be in different forms in the process of the invention: powder, shaped products, such as granules (for example extrudates or beads) or pellets, which are obtained by extrusion, pelletizing, moulding, compacting or any other type of known process. In practice, at the industrial level, it is the granule or bead forms which are most advantageous, both with regard to efficiency and with regard to convenience of use.

In accordance with the embodiment carried out in the gas phase in the presence of hydrofluoric acid, the ratio of the hydrofluoric acid to the compound of formula (II) may vary widely. Generally, the amount of hydrofluoric acid is in excess. Thus, the ratio of the number of moles of hydrofluoric acid to the number of moles of halogenated compound of formula (II) usually varies between 1 and 30. It is advantageously chosen between 6 and 12.

The process of the invention, carried out in the gas phase, is conducted at a high temperature, as a general rule above 50° C. It is recommended to work at temperatures between 50° C. and 400° C., preferably between 100° C. and 300° C.

For reasons of simplicity, the process of the invention is conducted at atmospheric pressure.

However, it is also possible to work at lower or higher pressures.

From a practical point of view, the process of the invention, carried out in the gas phase, may be carried out in batch mode or continuous mode.

Generally, the starting point is the mixing, in any manner, of the halogenated compound of formula (II) and the hydrofluoric acid. Thus, it is possible to mix said reactants, in a mixing zone, then send the mixture obtained to the catalytic bed.

When the process is carried out in batch mode, the amount of fluorination catalyst used, expressed as weight of catalyst per weight of the halogenated compound of formula (II) may vary, for example, between 0.1% and 20%, preferably between 0.5% and 5%.

The other variant of the invention consists in conducting the reaction in continuous mode, in a tubular or multitubular reactor comprising the solid catalyst arranged as a fixed bed. The amount of fluorination catalyst used, expressed as weight of catalyst per weight of the halogenated compound of formula (II), is preferably less than 0.1% by weight.

The halogenated compound of formula (II) and the hydrofluoric acid may be introduced into the reactor separately or as a mixture. As mentioned above, it is possible to mix them, in a mixing zone, then send the mixture obtained to the catalytic bed.

The reaction mixture passes through the catalytic bed, preferably from the bottom upwards.

The contact time, which is defined as the ratio between the bulk volume of catalyst and the flow rate of the gas stream, may vary widely, and is usually between 0.2 and 100 seconds.

The contact time is preferably chosen between 5 and 50 seconds.

The weight of substrate used per weight of catalyst and per hour generally varies between $0.01\ h^{-1}$ and $2\ h^{-1}$, preferably between $0.05\ h^{-1}$ and $0.5\ h^{-1}$.

At the end of the reaction, a gas phase is recovered that comprises the excess hydrofluoric acid, the hydrochloric acid formed by the reaction, and optionally the fluorinated compound of formula (I) depending on its boiling point. Said compound of formula (I), if it has a high boiling point, is found in the liquid phase via condensation. Preferably, said compound of formula (I) is present in the gas phase, in particular when it is trifluoromethanesulfonyl fluoride.

The compound of formula (I) is recovered from the reaction mixture according to any of the conventional techniques known to those skilled in the art. For example, the gas stream comprising the compound of formula (I) is brought into contact with water in which HF and HCl are absorbed. Said compound of formula (I) is easily and preferably recovered in liquid form via condensation.

According to another preferred embodiment of the process of the invention, according to which it is carried out in the liquid phase, the fluorinating agent used for reacting with the compound of formula (II) is hydrofluoric acid or at least an ionic fluoride of a monovalent or divalent cation.

In accordance with the embodiment according to which the process of the invention is carried out in the liquid phase in the presence of hydrofluoric acid, said process is performed using an antimony-based fluorination catalyst. In particular, said catalyst is selected from the antimony fluorides $SbF_3$, $SbF_4Cl$ and $SbF_5$, alone or as a mixture. Preferably, said catalyst essentially consists of the species $SbF_5$ or is a mixture of the species $SbF_3$ and $SbF_5$. Said catalyst may be a bulk catalyst or a catalyst supported on a support such as carbon black, graphite, alumina or a fluorinated alumina. The amount of fluorination catalyst used, expressed as weight of catalyst per weight of the halogenated compound of formula (II) is preferably less than between 0.01% and 10% by weight, preferably between 0.1% and 5% by weight.

The fluorination process according to the invention, carried out in the liquid phase, may be carried out in batch mode or continuous mode. It is carried out in the presence of one or more solvents, in particular an excess of hydrofluoric acid.

The implementation, in the liquid phase, of the preparation process according to the invention, in the presence of hydrofluoric acid, is carried out at a temperature between 0° C. and 300° C., preferably between 50° C. and 150° C. This implementation is carried out under autogenous pressure. The ratio of the number of moles of hydrofluoric acid to the number of moles of halogenated compound of formula (II) usually varies between 1 and 20. It is advantageously chosen between 3 and 10.

In accordance with the embodiment according to which the process of the invention is carried out in the liquid phase in the presence of an ionic fluoride of a monovalent or divalent cation, said monovalent ionic fluoride may be an alkali metal fluoride or a fluoride of an onium cation and said ionic fluoride of a divalent cation is preferably an alkaline-earth metal fluoride or a fluoride of a cation belonging to group IIB of the Periodic Table of the Elements. By subjecting the compound of formula (II) to an exchange reaction between said halogen atom(s) X present in said compound of formula (II) (X being other than fluorine) and the fluorine introduced by the ionic fluoride, the compound of formula (I) is prepared.

Preferably, said ionic fluoride of a monovalent cation is such that said monovalent cation is an alkali metal cation selected from lithium, sodium, potassium and caesium. Very preferably, it is potassium. Said ionic fluoride of a monovalent cation may also be a fluoride of an onium cation, that is to say an ammonium fluoride wherein the cation corresponds to the formula $N(R_4R_5R_6R_7)^+$ or a phosphonium fluoride wherein the cation corresponds to the formula $P(R_4R_5R_6R_7)^+$, $R_4$, $R_5$, $R_6$ and $R_7$, which are identical or different, are selected from a linear or branched alkyl group having 1 to 12 carbon atoms, preferably 1 to 4 carbon atoms, and a benzyl group.

By way of more specific examples, mention may be made of tetrabutylammonium fluoride, methyltri(n-butyl)ammonium fluoride, N-methyl-N,N,N-trioctylammonium fluoride, trimethylphenylphosphonium fluoride, tetrabutylphosphonium fluoride, methyltri(n-butyl)phosphonium fluoride, methyltri(isobutyl)phosphonium fluoride and diisobutyl-n-octylmethylphosphonium fluoride. Preferably, tetrabutylammonium fluoride and tetrabutylphosphonium fluoride are chosen.

Preferably, said ionic fluoride of a divalent cation is such that said cation is an alkaline-earth metal cation preferably selected from magnesium and calcium or a cation belonging to group IIB of the Periodic Table of the Elements, preferably zinc.

In accordance with the process of the invention carried out in the liquid phase, it is advantageous to use a mixture of ionic fluorides as defined above. In particular, it is advantageous to use a mixture of fluorides of monovalent cations, and very preferably a mixture of a potassium fluoride and of an onium fluoride as previously defined.

The amount of (monovalent and/or divalent) ionic fluoride used with respect to the amount of compound of formula (II) is preferably greater than the stoichiometry. The ratio of the number of fluoride moles to the number of halogen atoms to be exchanged from the compound (II) is advantageously between 1 and 20, preferably 4 to 10.

The process according to the invention performed in the liquid phase is carried out in an aqueous medium, in an aqueous-organic medium or in an organic medium.

The organic solvent present in the aqueous-organic medium or anhydrous organic medium is preferably a polar aprotic solvent, in particular in a sulfoxide solvent such as dimethylsulfoxide (DMSO), in an N,N-disubstituted amine solvent such as dimethylformamide (DMF), in a nitrile solvent such as acetonitrile or adiponitrile, in an ester solvent such as ethyl acetate, in a tertiary amine solvent such as triethylamine, in a nitrogen-containing heterocycle solvent such as pyridine, in a ketone solvent such as acetone or butanone, or in an organosulfur solvent such as sulfolane.

The process according to the invention performed in the liquid phase is carried out at a temperature between 80° C. and 400° C. It is conducted under regulated pressure or under autogenous pressure.

It may be carried out continuously or in batch mode.

The reactants used in the process according to the invention carried out in the liquid phase may be introduced in any order according to different variants.

When the process according to the invention is carried out in an aqueous or an aqueous-organic medium, one preferred embodiment consists in mixing water, to which an organic solvent has optionally been added, and at least one ionic fluoride as defined above in the present description, in particular potassium fluoride. This mixture is heated to the desired reaction temperature, in particular between 80° C. and 250° C., preferably between 100° C. and 180° C., and then said compound of formula (II) is introduced into said mixture. The reaction mixture is advantageously stirred throughout the period during which the heating is maintained. The compound of formula (II) is introduced pure, in solution in water or in said organic solvent or in a water-solvent mixture. Said compound of formula (II) can be introduced all at once, or gradually, in fractions. Another preferred embodiment of the process according to the invention, carried out in an aqueous or aqueous-organic medium, consists in simultaneously introducing at least ionic fluoride and said compound of formula (II) into water, to which an organic solvent has optionally been added, and then in heating said reaction mixture to the desired reaction temperature. The heating of the reaction mixture is maintained for a variable period of time. Preferably, the heating of the reaction mixture is maintained for a period of time of between 30 minutes and 48 hours, more preferably between 1 and 10 hours and even more preferably between 1 and 5 hours.

When the process according to the invention is carried out in an organic medium, one preferred embodiment consists in introducing the compound of formula (II), pure or present in solution in said polar aprotic solvent, into a suspension of at least one ionic fluoride in said solvent, said suspension having been previously heated to the chosen temperature, preferably between 200° C. and 400° C. The heating of the reaction mixture is maintained for a period of time that varies between 2 and 20 hours, preferably between 2 and 10 hours.

The compound of formula (I), obtained according to the process of the invention carried out in the liquid phase, is recovered from the reaction medium according to any of the conventional techniques known to those skilled in the art, for example by liquid-liquid extraction followed by purification by crystallization or distillation.

According to one particular embodiment of the process according to the invention, the fluorinating agent selected from hydrofluoric acid and an ionic fluoride of a monovalent or divalent cation is advantageously used in combination with a second fluorinating agent such as $F_2$ gas, sulfur tetrafluoride $SF_4$, sulfur hexafluoride $SF_6$ or thionyl fluoride $SOF_2$. The process of the invention could also be carried out simply using $F_2$ gas, sulfur tetrafluoride $SF_4$, sulfur hexafluoride $SF_6$ and/or thionyl fluoride $SOF_2$.

The process of the invention, carried out in the gas phase or liquid phase, is advantageously conducted in equipment capable of withstanding the corrosion of the reaction medium. For example, equipment formed from a graphite material or from fluoropolymers (in particular polytetrafluoroethylene PTFE, polyvinylidene fluoride PVDF and perfluoroalkyl resins PFA) is chosen. The equipment may also be formed from alloys based on molybdenum, chromium, cobalt, iron, copper, manganese, titanium, zirconium, aluminum, carbon and tungsten, sold under the Hastelloy® brands or the alloys of nickel, chromium, iron and manganese to which copper and/or molybdenum are added sold under the name Inconel® and more particularly the Hastelloy C 276 or Inconel 600, 625 or 718 alloys. It is also possible to choose stainless steels, such as austenitic steels [Robert H. Perry et al., *Perry's Chemical Engineers' Handbook, Sixth Edition* (1984), pages 23-44] and more particularly the 304, 304 L, 316 or 316 L stainless steels.

In accordance with the process of the invention, the compound of formula (II) is advantageously obtained by radical halogenation, preferably by radical chlorination, of a compound of formula $R'_H$—$SO_2X$ (formula III), where $R'_H$ is selected from the following groups
$R'_H1$, $R'_H2$ and $R'_H3$;
$R'_H1$=—$C_nH_{2n+1}$ with n=1-10; preferably n=1-5, very preferably n=1;
$R'_H2$=—$C_xH_{2x}$—$SO_2X$ with x=1-10; preferably x=1-5, very preferably x=1;
$R'_H3$=ϕ-$C_cH_{2c}$ with c=1-10; preferably c=1-5, very preferably c=1;
X being a halogen atom selected from chlorine and bromine.

More particularly, the radical chlorination of $R'_H1$-$SO_2X$ leads to the compound of formula R'1-$SO_2X$ being obtained, with R'1 as defined above. The radical chlorination of $R'_H2$-$SO_2X$ leads to the compound of formula R'2-$SO_2X$ being obtained, with R'2 as defined above. The radical chlorination of $R'_H3$-$SO_2X$ leads to the compound of formula R'3-$SO_2X$ being obtained, with R'3 as defined above. X is a halogen atom selected from chlorine and bromine.

Radical halogenation, preferably radical chlorination, is a process known to a person skilled in the art. A person skilled in the art could for example easily carry out a radical halogenation process from the teaching described in U.S. Pat. No. 2,674,620. The radical halogenation, preferably the radical chlorination, is carried out by photohalogenation, preferably by photochlorination.

The compound of formula (II) is more advantageously obtained by ionic halogenation, more particularly by ionic chlorination. A person skilled in the art could for example easily carry out an ionic halogenation process from the teaching described in U.S. Pat. No. 2,832,803.

Preferably, the compound of formula (III) is a compound of formula $R'_H1$-$SO_2X$ with $R'_H1$=—$C_nH_{2n+1}$, n=1 and X=Cl. Thus, the preparation of $CCl_3$—$SO_2Cl$ is carried out by radical chlorination of the mesyl chloride of formula $CH_3$—$SO_2Cl$.

The fluorinated compound of formula (I) prepared according to the process of the invention is advantageously used as a reactive compound for the synthesis of a sulfonimide compound (R—$SO_2)_2$NH and salts thereof (R—$SO_2)_2$NMe (Me representing an alkali metal) or of a fluorinated compound having a sulfonic acid function —$SO_2OH$ and having a formula R—$SO_2OH$, R having the definition specified above in the present description, namely selected from the groups R1, R2 and R3.

Another subject of the invention is a process for preparing a compound selected from the group consisting of a sulfonimide compound (R—$SO_2)_2$NH, salts thereof (R—$SO_2)_2$NMe (Me representing an alkali metal) and a fluorinated compound having a sulfonic acid function —$SO_2OH$ and having a formula R—$SO_2OH$, R having the definition specified above in the present description, said process comprising:
  a step of preparing a compound R—$SO_2F$ of formula (I) according to the process described above,
  a step wherein said fluorinated compound of formula (I) is used as a reactive compound for the synthesis of a sulfonimide compound (R—$SO_2)_2$NH and salts thereof (R—$SO_2)_2$NMe (Me representing an alkali metal) or of a fluorinated compound having a sulfonic acid function —$SO_2OH$ and having a formula R—$SO_2OH$, R having the definition specified above in the present description.

Another subject of the invention is therefore a process for preparing a salt of a sulfonimide compound of formula (R—$SO_2)_2$NMe from a fluorinated compound of formula (I) comprising:
  a) the preparation of a compound R—$SO_2F$ of formula (I) according to the process described above,
  b) a step of ammonolysis of R—$SO_2F$ to give (R—$SO_2)_2$NH, NR"$_3$;
  c) a step of acidification of (R—$SO_2)_2$NH, NR"$_3$ to give (R—$SO_2)_2$NH;
  d) a step of neutralization, with an alkali metal base, of (R—$SO_2)_2$NH to give (R—$SO_2)_2$NMe; and
  e) optionally a step of drying (R—$SO_2)_2$NMe,
wherein R is selected from the radicals R1, R2 and R3 defined above, R" represents a linear or branched alkyl group having from 1 to 20 carbon atoms and Me represents an alkali metal.

Preferably, Me is lithium.

Steps b), c), d) and e) are known to a person skilled in the art. In particular, the ammonolysis step is described in U.S. Pat. No. 5,723,664. The acidification, neutralization and drying steps are conventional steps that can be carried out under conditions known to a person skilled in the art.

Preferably, the fluorinated compound of formula (I) is trifluoromethanesulfonyl fluoride ($CF_3SO_2F$) so as to be able to use it in the synthesis of bis(trifluoromethanesulfonyl)imide of formula $(CF_3SO_2)_2NH$ and of lithium bis(trifluoromethanesulfonyl)imide of formula $(CF_3SO_2)_2NLi$ (LiTFSI).

In the case where the fluorinated compound of formula (I) is sulfonyl fluoride ($F-SO_2F$), it could be used in the synthesis of bis(fluorosulfonyl)imide of formula $(F-SO_2)_2NH$ and of lithium bis(fluorosulfonyl)imide of formula $(F-SO_2)_2NLi$ (LiFSI).

The sulfonimide compounds and salts thereof prepared according to the processes described above may advantageously be used as electrolyte salts, as antistatic agent precursors or else as surfactant precursors. In particular, said compounds may advantageously be used as electrolytes for the manufacture of batteries, in the field of electrochromism, electronics and electrochemistry. They are advantageously used as antistatic agents for the manufacture of pressure-sensitive adhesives (PSAs). As antistatic agents, they may also be used as components of lubricants. They are used in optical materials such as electroluminescent devices and are incorporated into the composition of photovoltaic panels. These uses are also subjects of the invention. In particular, one subject of the invention is a process for manufacturing an electrochemical device, preferably a battery, said process comprising a step of preparing a sulfonimide compound or salts thereof according to the process described above, and a step of manufacturing the electrochemical device in which the sulfonimide compound or salts thereof is (are) used as an electrolyte.

The compound of formula (I) prepared according to the process of the invention is more advantageously used for the preparation, via hydrolysis, of a fluorinated compound of formula $R-SO_2-OH$ where R is selected from the radicals R1, R2 and R3 defined above. For this purpose, the gas stream comprising the fluorinated compound of formula (I) resulting from the process of the invention, carried out in the gas phase, is for example brought into contact with an alkaline aqueous solution and then an acidification step is carried out in order to liberate the compound $R-SO_2-OH$, for example by using a solution of a strong mineral acid, such as sulfuric acid or hydrochloric acid.

Preferably, the fluorinated compound of formula (I) is trifluoromethanesulfonyl fluoride ($CF_3SO_2F$) so as to be able to use it in the synthesis of trifluoromethanesulfonic acid (also known as triflic acid) of formula $CF_3SO_2OH$.

The compound $R-SO_2-OH$ thus obtained is advantageously converted to an anhydride of formula $(R-SO_2)_2O$. The anhydrization reaction is known to a person skilled in the art and is particularly described in U.S. Pat. No. 8,222,450. Preferably, the fluorinated compound of formula (I) is trifluoromethanesulfonyl fluoride ($CF_3SO_2F$) so that the anhydrization of the triflic acid results in the production of the trifluoromethanesulfonic anhydride of formula $(CF_3SO_2)_2O$.

The present invention will now be described using non-limiting examples.

EXAMPLES 1 TO 7: PREPARATION OF TFSF VIA A FLUORINATION REACTION WITH HF IN THE GAS PHASE

Introduced into a Hastelloy C276 reactor consisting of a tube with a length of 60 cm and an external diameter of 2.5 cm, filled with a catalyst based on chromium oxide (~150 g) previously dried to constant weight and fluorinated, are trichloromethanesulfonyl chloride (TCSC), pure or dissolved in a solvent, at a flow rate of 0.05 mol/h of TCSC and anhydrous HF at a flow rate of 10 g/h. The solvent is trifluoromethylbenzene (TFMB), trifluoromethoxybenzene (TFMxB) or toluene.

The temperature is, depending on the test, set from 200° C. to 300° C. as an isotherm. Under these conditions, the residence time $t_r$ varies between 10 and 25 s.

After the reaction, the outgoing stream composed of trifluoromethanesulfonyl fluoride, HF and HCl is hydrolysed in potassium hydroxide bubblers mounted in series, and the various acids are assayed in the form of potassium salts by ion chromatography. The TFSF ($CF_3SO_2F$) is assayed in the form of potassium triflate ($CF_3SO_2K$).

The results obtained are shown in table (I).

The degree of conversion DC corresponds to the ratio between the number of moles of TCSC substrate converted and the number of moles of TCSC substrate employed.

The yield RY corresponds to the ratio between the number of moles of trifluoromethanesulfonyl fluoride TFSF product formed and the number of moles of TCSC substrate employed.

The yield CY corresponds to the ratio between the number of moles of TFSF product formed and the number of moles of TCSC substrate converted.

TABLE (I)

| Ref. ex | Solvent | T° C. | $t_r$ (s) | HF/TCSC (mol) | DC % | RY % | CY % |
|---|---|---|---|---|---|---|---|
| 1 | — | 250 | 22 | 10.8 | 82 | 75 | 91 |
| 2 | — | 250 | 11.5 | 21 | 50 | 47 | 94 |
| 3 | TFMB | 250 | 18 | 11 | 74 | 70 | 95 |
| 4 | TFMxB | 250 | 12.6 | 10.7 | 45 | 42 | 93 |
| 5 | toluene | 250 | 12.3 | 10.9 | 46 | 41 | 89 |
| 6 | — | 200 | 25 | 10.2 | 42 | 41 | 97 |
| 7 | — | 300 | 20.3 | 10.6 | 98 | 80 | 82 |

EXAMPLE 8: PREPARATION OF TFSF VIA A FLUORINATION REACTION WITH HF IN THE LIQUID PHASE

Charged to a 280 ml capacity Hastelloy C276 autoclave are:
TCSC: 110 g (0.5 mol)
HF: 40 g (2 mol, i.e. ~4 eq.)
$SbCl_5$: 5 g (0.02 mol, i.e. ~1 mol % with respect to HF)

The autoclave is brought to 120° C. for 3 h under autogenous pressure, then cooled to 20° C. and degassed in potassium hydroxide bubblers mounted in series; the residual reaction medium is drawn off and scrubbed in aqueous potassium hydroxide.

The potassium hydroxide aqueous phases are combined and analysed by $^{19}F$ NMR; trifluoromethanesulfonyl fluoride (TFSF), assayed in the form of potassium triflate (TAK of formula $CF_3SO_3K$), is obtained with a yield of 23%.

EXAMPLE 9: PREPARATION OF TFSF VIA A FLUORINATION REACTION WITH KF

Example 9.1: In a Polar Aprotic Solvent

Introduced into an autoclave made of stainless steel of grade 316L and having a capacity of 150 ml are:
KF: 29 g
TCSC: 22 g
Adiponitrile: 60 ml The autoclave is sealed and brought to 230° C. under autogenous pressure for 4 h, then cooled to 20° C. and degassed in potassium hydroxide bubblers mounted in series; the residual reaction medium is drawn off and scrubbed in aqueous potassium hydroxide. The potassium hydroxide aqueous phases are combined and analysed by $^{19}$F NMR; trifluoromethanesulfonyl fluoride, assayed in the form of potassium triflate (TAK), is obtained with a yield of 47%.

Example 9.2: In Water

Introduced into a perfectly stirred glass reactor having a capacity of 100 ml are:
KF: 32.6 g
TCSC: 12 g
water: 20 ml
The medium is brought to boiling, with stirring, for 1 h, then cooled and brought to neutral pH by addition of aqueous potassium hydroxide.
Analysis of the medium by $^{19}$F NMR shows that the potassium triflate (TAK) was formed with a yield of 63%.

EXAMPLE 10: PREPARATION OF DFSF ($CHF_2SO_2F$) VIA A FLUORINATION REACTION WITH HF IN THE GAS PHASE

The reaction is carried out under the same conditions as example 1, with the following charges and conditions:
DCSC ($CHCl_2SO_2Cl$): 0.05 mol/h
HF: 10 g/h (HF/DCSC ratio: 10)
The temperature is set at 250° C. as an isotherm and the residence time $t_r$ is 22 s.
The degree of conversion DC of the DCSC is 65% and the yield RY of DFSF is 42%.

EXAMPLE 11: PREPARATION OF DIFLUOROMETHANEDISULFONYL DIFLUORIDE ($DF_2DS$: ($CF_2DS$: ($CF_2(SO_2F)_2$) VIA A FLUORINATION REACTION WITH HF IN THE LIQUID PHASE

The reaction is carried out under the same conditions as example 8, with the following charges and conditions:
($CCl_2(SO_2Cl)_2$): 100 g (0.35 mol)
HF: 40 g (2 mol, i.e. ~6 eq.)
After reacting for 3 h at 120° C., the reaction medium is treated according to example 8.
$DF_2DS$ is obtained with a yield of 28%.

EXAMPLE 12: PREPARATION OF α,α-DIFLUOROBENZYLSULFONYL FLUORIDE (DFBSF: $C_6H_5CF_2SO_2F$) VIA A FLUORINATION REACTION WITH HF IN THE LIQUID PHASE

The reaction is carried out under the same conditions as example 8, with the following charges and conditions:
$C_6H_5CCl_2SO_2Cl$: 100 g (0.4 mol)
HF: 40 g (2 mol, i.e. ~5 eq.)
After reacting for 4 h at 150° C., the reaction medium is treated according to example 8.
DFBSF is obtained with a yield of 19%.

The invention claimed is:
1. A non-electrochemical process for preparing a fluorinated compound of formula (I) comprising at least one —$SO_2F$ function, wherein the compound of formula (I) is prepared by reacting a compound of formula (II) with at least one fluorinating agent, wherein the process is carried out in the gas phase and wherein the fluorinating agent is hydrofluoric acid:

R—$SO_2F$ (I)

wherein R is selected from the group consisting of R1, R2 and R3:
R1=-$C_nH_aF_b$ with n=1-10, a+b=2n+1, b≥1;
R2=-$C_xH_yF_z$—$SO_2F$ with x=1-10, y+z=2x and z≥1;
R3=Φ-$C_cH_hF_f$ with c=1-10; h+f=2c and f≥1; Φ denoting a phenyl group;

R'—$SO_2X$ (II)

wherein R' is selected from the group consisting of R'1, R'2 and R'3:
R'1=-$C_nH_aX_b$ with n=1-10, a+b=2n+1, b≥1;
R'2=-$C_xH_yX_z$—$SO_2X$ with x=1-10, y+z=2x and z≥1;
R'3=Φ-$C_cH_hX_f$ with c=1-10; h+f=2c and f≥1; Φ denoting a phenyl group; and
X is a halogen atom selected from the group consisting of chlorine and bromine.

2. The preparation process as claimed in claim 1, wherein the radicals R1 and R'1 are perhalogenated so that b=3 and a=0.

3. The preparation process as claimed in claim 1, wherein the radical R of the compound (I) is the radical R1 wherein n=1, a=0 and b=3, or n=1, a=1, b=2 or else n=1, a=2 and b=1.

4. The preparation process as claimed in claim 1, wherein the process uses at least one fluorination catalyst comprising chromium, zinc, nickel, a mixture of chromium and zinc, or a mixture of chromium and nickel.

5. The preparation process as claimed in claim 1, wherein the ratio of the number of moles of hydrofluoric acid to the number of moles of halogenated compound of formula (II) varies between 1 and 30.

6. The preparation process as claimed in claim 1, wherein the compound of formula (II) is obtained by radical halogenation of a compound of formula R'$_H$—$SO_2X$ (formula III), wherein R'$_H$ is selected from the group consisting of R'$_H$1, R'$_H$2 and R'$_H$3:
R'$_H$1=-$C_nH_{2n+1}$ with n=1-10;
R'$_H$2=-$C_xH_{2x}$—$SO_2X$ with x=1-10;
R'$_H$3=Φ-$C_cH_{2c}$ with c=1-10; and
X is a halogen atom selected from the group consisting of chlorine and bromine.

7. A process for preparing a compound selected from the group consisting of a sulfonimide compound (R—$SO_2$)$_2$NH and salts thereof, (R—$SO_2$)$_2$NMe, and a fluorinated compound having a sulfonic acid function —$SO_2OH$ and having a formula R—$SO_2OH$, said process comprising:
a step of preparing a compound R—$SO_2F$ of formula (I) as claimed in claim 1,
a step wherein said fluorinated compound of formula (I) is used as a reactive compound for the synthesis of a sulfonimide compound (R—$SO_2$)$_2$NH and salts thereof, (R—$SO_2$)$_2$NMe, or of a fluorinated compound having a sulfonic acid function —$SO_2OH$ and having a formula R—$SO_2OH$,
wherein R is selected from the group consisting of R1, R2 and R3:
R1=-$C_nH_aF_b$ with n=1-10, a+b=2n+1, b≥1;
R2=-$C_xH_yF_z$—$SO_2F$ with x=1-10, y+z=2x and z≥1; and
R3=Φ-$C_cH_hF_f$ with c=1-10; h+f=2c and f≥1; 1 denoting a phenyl group.

8. The process as claimed in claim 7, wherein the compound synthesized is selected from the group consisting of bis(trifluoromethanesulfonyl)imide of formula $(CF_3SO_2)_2NH$ and lithium bis(trifluoromethanesulfonyl)imide of formula $(CF_3SO_2)_2NLi$ (LiTFSI).

9. The process as claimed in claim 7, wherein the compound synthesized is trifluoromethanesulfonic acid of formula $CF_3SO_2OH$.

\* \* \* \* \*